US012721874B2

(12) United States Patent
Lee et al.

(10) Patent No.: US 12,721,874 B2
(45) Date of Patent: Sep. 1, 2026

(54) METHOD FOR IMPROVING PREPARATION OF FERMENTED BLACK GINSENG CONTAINING HIGH CONTENT OF FUNCTIONAL INGREDIENTS BASED ON SAFETY BY APPLYING LED

(71) Applicant: NATURE BIO PHARMA CO, Seoul (KR)

(72) Inventors: Seung Jin Lee, Jeju-do (KR); Joong Hyeok Lee, Gyeonggi-do (KR)

(73) Assignee: NATURE BIO PHARMA CO, Seoul (KR)

( * ) Notice: Subject to any disclaimer, the term of this patent is extended or adjusted under 35 U.S.C. 154(b) by 868 days.

(21) Appl. No.: 18/063,846

(22) Filed: Dec. 9, 2022

(65) Prior Publication Data

US 2023/0241147 A1 Aug. 3, 2023

(30) Foreign Application Priority Data

Dec. 9, 2021 (KR) ........................ 10-2021-0175835

(51) Int. Cl.

*A61K 36/258* (2006.01)
*A61K 31/704* (2006.01)
*A61P 31/14* (2006.01)
*C12N 1/14* (2006.01)
*C12P 33/00* (2006.01)
*C12R 1/685* (2006.01)

(52) U.S. Cl.

CPC .......... *A61K 36/258* (2013.01); *A61K 31/704* (2013.01); *A61P 31/14* (2018.01); *C12N 1/14* (2013.01); *C12P 33/00* (2013.01); *A61K 2236/13* (2013.01); *A61K 2236/17* (2013.01); *A61K 2236/19* (2013.01); *A61K 2236/51* (2013.01); *C12R 2001/685* (2021.05)

(58) Field of Classification Search

CPC ................ A61K 36/258; A61K 31/704; A61K 2236/13; A61K 2236/17; A61K 2236/19; A61K 2236/51; A61P 31/14; C12N 1/14; C12P 33/00; C12R 2001/685

See application file for complete search history.

(56) References Cited

FOREIGN PATENT DOCUMENTS

| | | | | | |
|---|---|---|---|---|---|
| KR | 20090106303 | A | * 10/2009 | ............ | A23L 19/03 |
| KR | 1020180040784 | A | 7/2018 | | |
| KR | 10-1972083 | B1 | 4/2019 | | |
| KR | 10-2052530 | B1 | 12/2019 | | |
| KR | 10-2297181 | B1 | 9/2021 | | |
| WO | WO-2007133054 | A1 | * 11/2007 | ............ | A23L 19/00 |
| WO | WO 2021/186453 | A | 9/2021 | | |

OTHER PUBLICATIONS

Hong, Seung-Beom, Dae-Ho Kim, and Robert A. Samson. "Aspergillus associated with Meju, a fermented soybean starting material for traditional soy sauce and soybean paste in Korea." Mycobiology 43.3 (2015): 218-224. (Year: 2015).*

Metwaly, Ahmed M., et al. "Black ginseng and its saponins: Preparation, phytochemistry and pharmacological effects." Molecules 24.10 (2019): 1856. (Year: 2019).*

Park ("Increase in the contents of ginsenosides in raw ginseng roots in response to exposure to 450 and 470 nm light from light-emitting diodes." Journal of Ginseng Research 36.2 (2012): 198). (Year: 2012).*

Li ( Anti-obesity Effects of Fermented Ginseng Root and Berry in Mice Fed a High-Fat Diet. Diss., 2017). (Year: 2017).*

Park et al., Cumulative Production of Bioactive Rg3, Rg5, Rk1, and CK from Fermented Black Ginseng Using Novel *Aspergillus niger* KHNT-1 Strain Isolated from Korean Traditional Food, *Processes*, 9, 227, 2021.

Han et al., "In Vitro Evaluation of Anti-Lung Cancer and Anti-COVID-19 Effects using Fermented Black Color Ginsent Extract", *Natural Product Communications*, vol. 16(9): 1-9, 2021.

* cited by examiner

*Primary Examiner* — Robert J Yamasaki
*Assistant Examiner* — Trevor Kane
(74) *Attorney, Agent, or Firm* — Revolution IP, PLLC

(57) ABSTRACT

The present invention relates to a method for improving the preparation of fermented black color ginseng containing functional ingredients at high contents based on safety, specifically to a novel *Aspergillus niger* KHNT-1 strain deposited with accession number KCTC14739BP; an improved process for preparing fermented black color ginseng through treatment with the strain, steaming utilizing pottery, and drying utilizing an LED dryer; fermented black color ginseng containing functional ingredients, ginsenosides Rg5, Rg3, and Rk1, and CK at high contents; and a composition for preventing, improving, or treating coronavirus infectious disease, the composition containing the fermented black color ginseng as an active ingredient.

As the fermented black color ginseng is prepared through fermentation using the novel *Aspergillus niger* KHNT-1 strain according to the present invention, steaming utilizing pottery as a steamer, and drying (fermentation) utilizing a medical LED as a dryer/fermenter, the method for improving the preparation of fermented black color ginseng is economical and safe since the preparation process takes 7 to 15 days and benzopyrene is not detected in the fermented black color ginseng, and the fermented black color ginseng contains ginsenosides Rg3, Rg5, and Rk1, and CK at high contents, and can be usefully utilized as a high value-added new drug raw material that is required to be contained at a high content per unit and in the field of high-functional food development.

9 Claims, 10 Drawing Sheets

[FIG. 1]
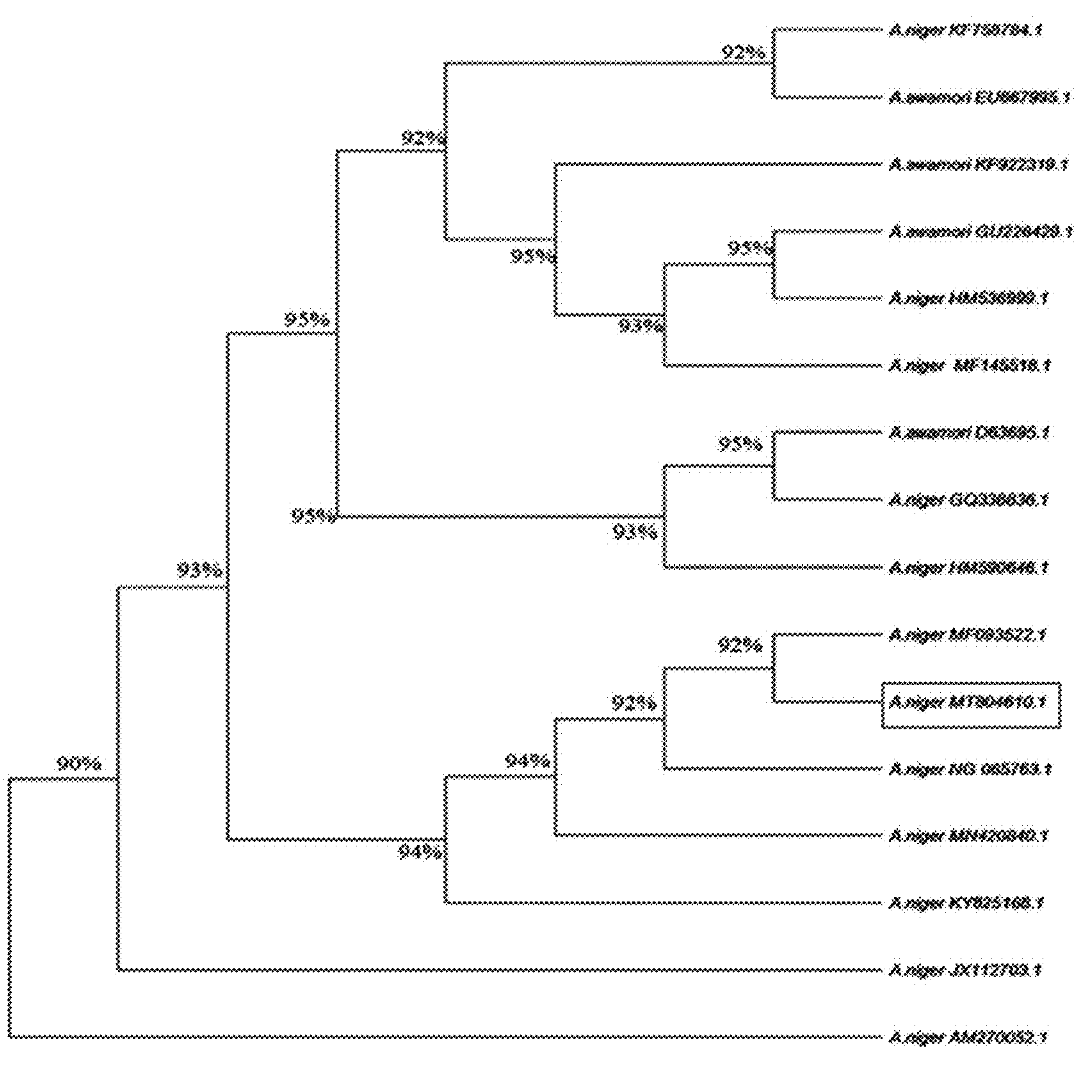

[FIG. 2]

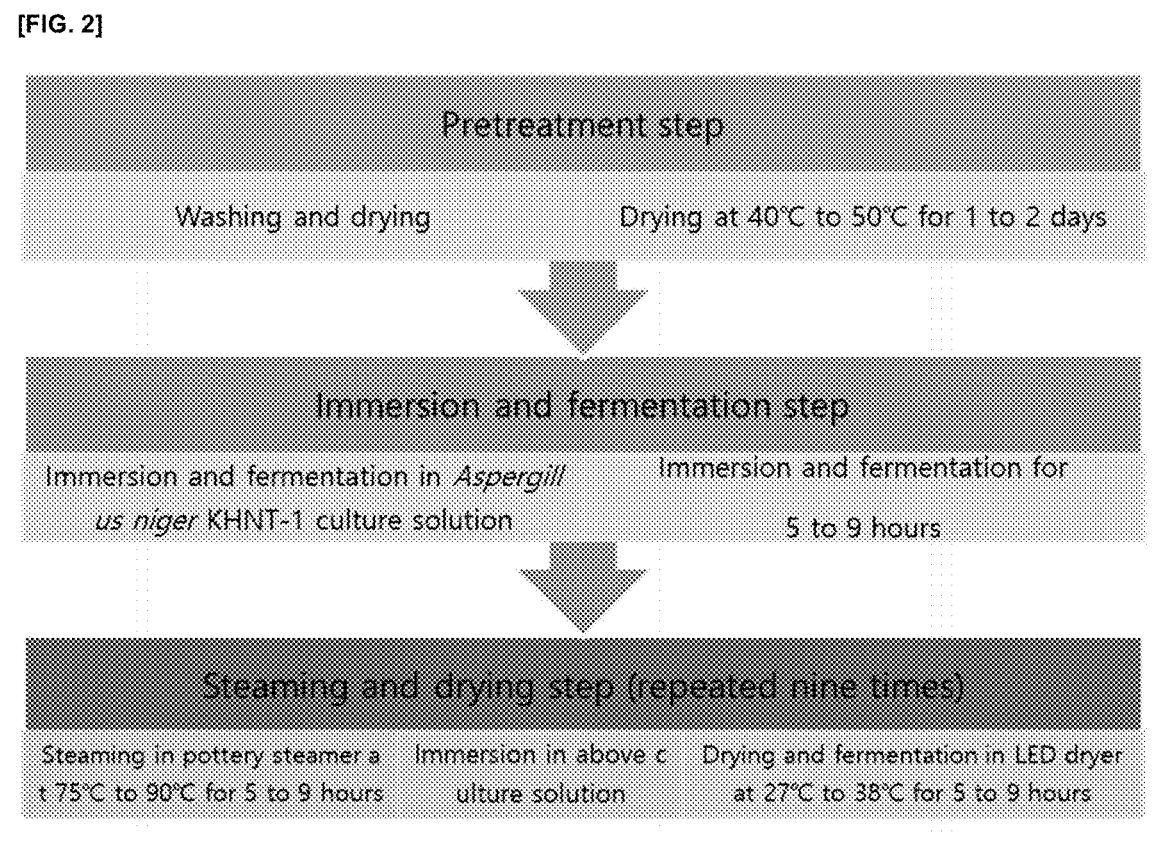

Pretreatment step

Washing and drying | Drying at 40℃ to 50℃ for 1 to 2 days

↓

Immersion and fermentation step

Immersion and fermentation in *Aspergillus niger* KHNT-1 culture solution | Immersion and fermentation for 5 to 9 hours

↓

Steaming and drying step (repeated nine times)

Steaming in pottery steamer at 75℃ to 90℃ for 5 to 9 hours | Immersion in above culture solution | Drying and fermentation in LED dryer at 27℃ to 38℃ for 5 to 9 hours

[FIG. 3A]

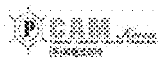

Test Certificate

| File No. | PCAM – Y21 – 396 |
|---|---|
| Page(s) | (1) / (Total 1) |

(Postcode 34036) 12, Techno 11-ro (Tamnip-dong 867), Yuseong-gu, Daejeon, Republic of Korea / Contact No. (042) 823-8680~1 / Fax No. (042) 823-8682

1. Sample Information

| **Name of Institution** | Nature Bio Pharma Co., Ltd. | Request Date | May 13, 2021 |
|---|---|---|---|
| **Name of Sample** | Fermented Black Panax Ginseng (BLACK 9) 9-times-steamed-and-9-times-fermented (LED Device Drying System) | | |
| **Production Site/Address** | Punggi-eup, Yeongju-si, Gyeongsangbuk-do, Republic of Korea | | |
| **Producer** | Nature Bio Pharma Co., Ltd. | **Test Location** | Laboratory (Analysis Room) |
| **Duration of Test** | May 13, 2021 to May 17, 2021 | **Analysis Equipment** | HPLC |
| **Usage** | For Submission | **Test Environment Temperature** | 22 to 24 °C |
| | | **Test Environment Humidity** | 70% R.H. and lower |

2. Test Result(s)

| Test Item: 1 Ingredient | | |
|---|---|---|
| Benzopyrene | | |
| **Result(s) (mg/L)** | Above item(s) not detected. | |
| **Confirmation** | **Author (Tester)** | **Approbator (Technical Manager)** |
| | Name: Eun-ji KANG | Name: Ju-hong PARK |

*The analysis result(s) above may not be used as supporting evidence for legal requirements concerning publicity/advertisement/lawsuit.
*The analysis result(s) above is/are the result(s) of the sample(s) submitted by the applicant, and the name of the sample(s) was/were suggested by the applicant.
*Use of this test certificate for other purposes is strictly prohibited.

May 17, 2021

PCAM KOREA, Inc.

[FIG. 3B]

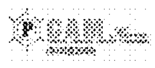

Test Certificate

| File No. | PCAM – Y21 – 818(1) |
| --- | --- |
| Page(s) | (1) / (Total 1) |

(Postcode 34036) 12, Techno 11-ro (Tamnip-dong 867), Yuseong-gu, Daejeon, Republic of Korea / Contact No. (042) 823-8680~1 / Fax No. (042) 823-8682

1. Sample Information

| **Name of Institution** | Nature Bio Pharma Co., Ltd. | **Request Date** | September 7, 2021 |
| --- | --- | --- | --- |
| **Name of Sample** | 14 Steamed-Fermented Black Panax Ginseng (BLACK9) - Special wavelength Lighting. (LED) | | |
| **Production Site/Address** | Punggi-eup, Yeongju-si, Gyeongsangbuk-do, Republic of Korea | | |
| **Producer** | Nature Bio Pharma Co., Ltd. | **Test Location** | Laboratory (Analysis Room) |
| **Duration of Test** | September 7, 2021 to September 10, 2021 | **Analysis Equipment** | HPLC |
| **Usage** | For Submission | **Test Environment Temperature** | 22 to 24 °C |
| | | **Test Environment Humidity** | 70% R.H. and lower |

2. Test Result(s)

| Test Item: 1 Ingredient | | |
| --- | --- | --- |
| Benzopyrene | | |
| **Result(s) (mg/L)** | Above item(s) not detected. | |
| **Confirmation** | **Author (Tester)** | **Approbator (Technical Manager)** |
| | Name: Eun-ji KANG | Name: Ju-hong PARK |

*The analysis result(s) above may not be used as supporting evidence for legal requirements concerning publicity/advertisement/lawsuit.
*The analysis result(s) above is/are the result(s) of the sample(s) submitted by the applicant, and the name of the sample(s) was/were suggested by the applicant.
*Use of this test certificate for other purposes is prohibited.

September 10, 2021

PCAM KOREA, Inc.

[FIG. 4A]

Test Certificate

| File No. | PCAM – Y21 – 387(1) |
| --- | --- |
| Page(s) | (1) / (Total 1) |

(Postcode 34036) 12, Techno 11-ro (Tamnip-dong 867), Yuseong-gu, Daejeon, Republic of Korea / Contact No. (042) 823-8680~1 / Fax No. (042) 823-8682

1. Sample Information

| **Name of Institution** | Nature Bio Pharma Co., Ltd. | **Request Date** | May 11, 2021 |
| --- | --- | --- | --- |
| | | **Producer** | Nature Bio Pharma Co., Ltd. |
| **Name of Sample** | Fermented Black Panax Ginseng (BLACK9) LED Device (“Natur” Microorganism (*Aspergillus sp.* KHNT-1) Treatment | | |
| **Production Site/Address** | Punggi-eup, Yeongju-si, Gyeongsangbuk-do, Republic of Korea | **Test Location** | Laboratory (Analysis Room) |
| **Duration of Test** | May 11, 2021 to May 17, 2021 | **Analysis Equipment** | LC-MS/MS |
| **Usage** | For Submission | **Test Environment Temperature** | 22 to 24 °C |
| | | **Test Environment Humidity** | 70% R.H. and lower |

2. Test Result(s)

Test result(s) (Measured Value(s))

| Compound | Content |
| --- | --- |
| | Fermented Black Panax Ginseng (BLACK9) LED Device (“Natur” Microorganism (*Aspergillus sp.* KHNT-1) Treatment |
| Rg3(S) | 9,245.49 |
| Rg3(R) | 4,961.90 |
| C-K | 34.10 |
| Rk1 | 11,764.54 |
| Rg5 | 16,346.40 |

Unit: mg/kg

| Confirmation | Author (Tester) | Approbator (Technical Manager) |
| --- | --- | --- |
| | Name: Eun-ji KANG | Name: Sun-ol KIM |

*The analysis result(s) above may not be used as supporting evidence for legal requirements concerning publicity/advertisement/lawsuit.

*The analysis result(s) above is/are the result(s) of the sample(s) submitted by the applicant, and the name of the sample(s) was/were suggested by the applicant.

*Use of this test certificate for other purposes is prohibited.

May 17, 2021

PCAM KOREA, Inc.

[FIG. 4B]

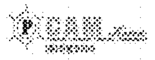

Test Certificate

| File No. | PCAM – Y21 – 387(2) |
|---|---|
| Page(s) | (1) / (Total 1) |

(Postcode 34036) 12, Techno 11-ro (Tamnip-dong 867), Yuseong-gu, Daejeon, Republic of Korea / Contact No. (042) 823-8680~1 / Fax No. (042) 823-8682

1. Sample Information

| **Name of Institution** | Nature Bio Pharma Co., Ltd. | **Request Date** | May 11, 2021 |
|---|---|---|---|
| | | **Producer** | Nature Bio Pharma Co., Ltd. |
| **Name of Sample** | Fermented Black Panax Ginseng (BLACK9) LED Device (*Lactobacillus plantarum* Treatment) | | |
| **Production Site/Address** | Punggi-eup, Yeongju-si, Gyeongsangbuk-do, Republic of Korea | **Test Location** | Laboratory (Analysis Room) |
| **Duration of Test** | May 11, 2021 to May 17, 2021 | **Analysis Equipment** | LC-MS/MS |
| **Usage** | For Submission | **Test Environment Temperature** | 22 to 24 °C |
| | | **Test Environment Humidity** | 70% R.H. and lower |

2. Test Result(s)

Test result(s) (Measured Value(s))

| Compound | Content |
|---|---|
| | Fermented Black Panax Ginseng (BLACK9) LED Device (*Lactobacillus plantarum* Treatment) |
| Rg3(S) | 7,634.60 |
| Rg3(R) | 3,380.41 |
| C-K | 26.48 |
| Rk1 | 6,425.42 |
| Rg5 | 9,756.40 |

Unit: mg/kg

| **Confirmation** | **Author (Tester)** | **Approbator (Technical Manager)** |
|---|---|---|
| | Name: Eun-ji KANG | Name: Sun-ol KIM |

*The analysis result(s) above may not be used as supporting evidence for legal requirements concerning publicity/advertisement/lawsuit.
*The analysis result(s) above is/are the result(s) of the sample(s) submitted by the applicant, and the name of the sample(s) was/were suggested by the applicant.
*Use of this test certificate for other purposes is prohibited.

May 17, 2021

PCAM KOREA, Inc.

[FIG. 4C]

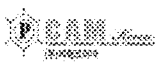

Test Certificate

| File No. | PCAM – Y21 – 387(3) |
|---|---|
| Page(s) | (1) / (Total 1) |

(Postcode 34036) 12, Techno 11-ro (Tamnip-dong 867), Yuseong-gu, Daejeon, Republic of Korea / Contact No. (042) 823-8680~1 / Fax No. (042) 823-8682

1. Sample Information

| | | | |
|---|---|---|---|
| **Name of Institution** | Nature Bio Pharma Co., Ltd. | **Request Date** | May 11, 2021 |
| | | **Producer** | Nature Bio Pharma Co., Ltd. |
| **Name of Sample** | Fermented Black Panax Ginseng (BLACK9) LED Device (Water Treatment) | | |
| **Production Site/Address** | Punggi-eup, Yeongju-si, Gyeongsangbuk-do, Republic of Korea | **Test Location** | Laboratory (Analysis Room) |
| **Duration of Test** | May 11, 2021 to May 17, 2021 | **Analysis Equipment** | LC-MS/MS |
| **Usage** | For Submission | **Test Environment Temperature** | 22 to 24 °C |
| | | **Test Environment Humidity** | 70% R.H. and lower |

2. Test Result(s)

Test result(s) (Measured Value(s))

| Compound | Content<br>Fermented Black Panax Ginseng (BLACK9) LED Device (Water Treatment) |
|---|---|
| Rg3(S) | 6,724.20 |
| Rg3(R) | 3,757.48 |
| C-K | 32.21 |
| Rk1 | 7,151.53 |
| Rg5 | 11,246.04 |

Unit: mg/kg

| Confirmation | Author (Tester) | Approbator (Technical Manager) |
|---|---|---|
| | Name: Eun-ji KANG | Name: Sun-ol KIM |

*The analysis result(s) above may not be used as supporting evidence for legal requirements concerning publicity/advertisement/lawsuit.
*The analysis result(s) above is/are the result(s) of the sample(s) submitted by the applicant, and the name of the sample(s) was/were suggested by the applicant.
*Use of this test certificate for other purposes is prohibited.

May 17, 2021

PCAM KOREA, Inc.

[FIG. 4D]

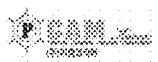

Test Certificate

| File No. | PCAM – Y21 – 387(4) |
|---|---|
| Page(s) | (1) / (Total 1) |

(Postcode 34036) 12, Techno 11-ro (Tamnip-dong 867), Yuseong-gu, Daejeon, Republic of Korea / Contact No. (042) 823-8680~1 / Fax No. (042) 823-8682

1. Sample Information

| **Name of Institution** | Nature Bio Pharma Co., Ltd. | **Request Date** | May 11, 2021 |
|---|---|---|---|
| | | **Producer** | Nature Bio Pharma Co., Ltd. |
| **Name of Sample** | Fermented Black Panax Ginseng (BLACK9) LED Device (No Treatment) | | |
| **Production Site/Address** | Punggi-eup, Yeongju-si, Gyeongsangbuk-do, Republic of Korea | **Test Location** | Laboratory (Analysis Room) |
| **Duration of Test** | May 11, 2021 to May 17, 2021 | **Analysis Equipment** | LC-MS/MS |
| **Usage** | For Submission | **Test Environment Temperature** | 22 to 24 °C |
| | | **Test Environment Humidity** | 70% R.H. and lower |

2. Test Result(s)

Test result(s) (Measured Value(s))

| Compound | Content |
|---|---|
| | Fermented Black Panax Ginseng (BLACK9) LED Device (No Treatment) |
| Rg3(S) | 7,752.09 |
| Rg3(R) | 3,248.11 |
| C-K | 52.27 |
| Rk1 | 8,009.52 |
| Rg5 | 11,566.93 |

Unit: mg/kg

| **Confirmation** | **Author (Tester)** | **Approbator (Technical Manager)** |
|---|---|---|
| | Name: Eun-ji KANG | Name: Sun-ol KIM |

*The analysis result(s) above may not be used as supporting evidence for legal requirements concerning publicity/advertisement/lawsuit.
*The analysis result(s) above is/are the result(s) of the sample(s) submitted by the applicant, and the name of the sample(s) was/were suggested by the applicant.
*Use of this test certificate for other purposes is prohibited.

May 17, 2021

PCAM KOREA, Inc.

[FIG. 4E]

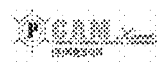

Test Certificate

| File No. | PCAM – Y20 – 473 |
| --- | --- |
| Page(s) | (1) / (Total 1) |

(Postcode 34036) 12, Techno 11-ro (Tamnip-dong 867), Yuseong-gu, Daejeon, Republic of Korea / Contact No. (042) 823-8680~1 / Fax No. (042) 823-8682

1. Sample Information

| **Name of Institution** | Nature Bio Pharma Co., Ltd. | **Request Date** | May 18, 2021 |
| --- | --- | --- | --- |
| | | **Test Client** | Nature Bio Pharma Co., Ltd. |
| **Production Site/Address** | Punggi-eup, Yeongju-si, Gyeongsangbuk-do, Republic of Korea | | |
| **Name of Sample** | Fermented Black Panax Ginseng | **Test Location** | Laboratory (Analysis Room) |
| **Duration of Test** | May 18, 2021 to June 1, 2021 | **Analysis Equipment** | LC-MS/MS |
| **Usage** | For Submission | **Test Environment Temperature** | 22 to 24 °C |
| | | **Test Environment Humidity** | 70% R.H. and lower |

2. Test Result(s)

Test result(s) (Measured Value(s))

| Compound | Content |
| --- | --- |
| | Fermented Black Panax Ginseng |
| Rg3(S) | 2,533.39 |
| Rg3(R) | 2,042.42 |
| C-K | 29.26 |
| Rk1 | 1,999.41 |
| Rg5 | 3,262.77 |

Unit: mg/kg

| **Confirmation** | **Author (Tester)** | **Approbator (Technical Manager)** |
| --- | --- | --- |
| | Name: Seul-ki KIM | Name: Sun-ol KIM |

*The analysis result(s) above may not be used as supporting evidence for legal requirements concerning publicity/advertisement/lawsuit.
*The analysis result(s) above is/are the result(s) of the sample(s) submitted by the applicant, and the name of the sample(s) was/were suggested by the applicant.
*Use of this test certificate for other purposes is prohibited.

June 1, 2021

PCAM KOREA, Inc.

[FIG. 5]
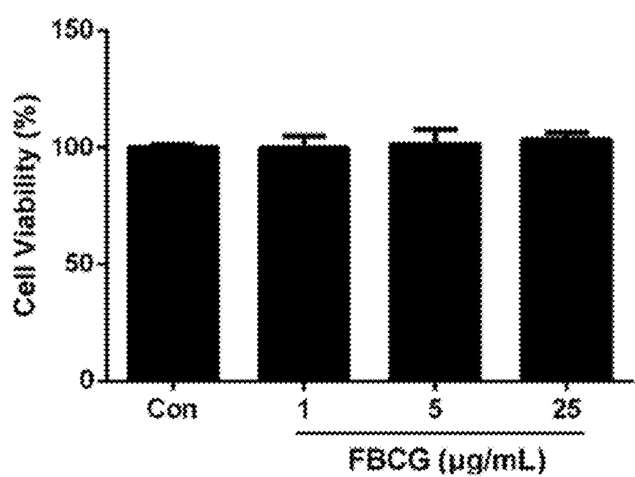
[FIG. 6A]
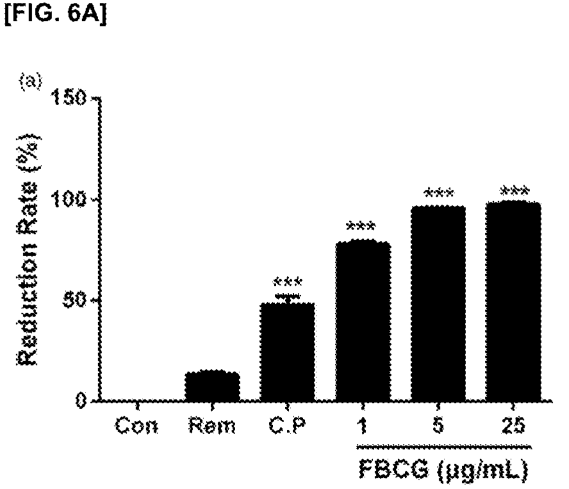
[FIG. 6B]
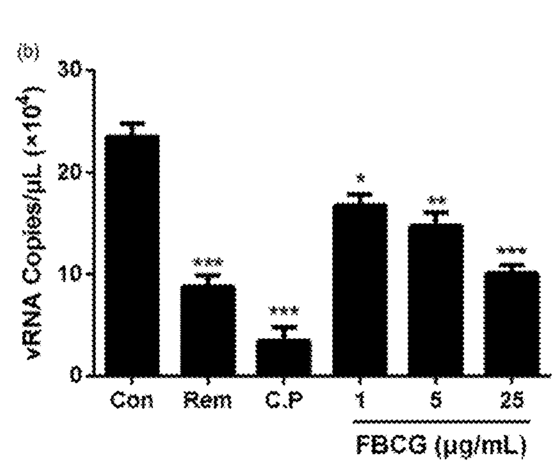

METHOD FOR IMPROVING PREPARATION OF FERMENTED BLACK GINSENG CONTAINING HIGH CONTENT OF FUNCTIONAL INGREDIENTS BASED ON SAFETY BY APPLYING LED

This application claims priority to Korean Patent application No. 10-2021-0175835, entitled "A method for improving preparation of fermented black ginseng containing high content of functional ingredients based on safety by applying LED," filed on Dec. 9, 2021.

TECHNICAL FIELD

The present invention relates to a method for improving the preparation of fermented black color ginseng containing functional ingredients at high contents based on safety, specifically to a novel *Aspergillus niger* KHNT-1 strain deposited with accession number KCTC14739BP; an improved process for preparing fermented black color ginseng through treatment with the strain, steaming utilizing pottery, and drying utilizing an LED dryer; fermented black color ginseng containing functional ingredients, ginsenosides Rg5, Rg3, and Rk1, and Compound K (CK) at high contents; and a composition for preventing, improving; or treating coronavirus infectious disease, which contains the fermented black color ginseng as an active ingredient.

BACKGROUND ART

Korean ginseng (*Panax ginseng* C. A. Meyer) is a perennial herb belonging to the genus *Panax* of the family Araliaceae, and the root of Korean ginseng is called ginseng radix in oriental medicine and is used for medicinal purposes. Ginseng has different activities depending on its biological conversion, and this biological conversion may lead to two major classifications depending on the active ingredients of ginseng, namely protopanaxatriol (PPT) and protopanaxadiol (PPD). The biological activities of PPT and PPD are different depending on the number and location of sugar moieties linked to aglycone. The deglycosylation rate of the sugar determines the effect of ginsenosides on human metabolism.

Ginsenosides are linked to polymeric components, and are not absorbed into the body without being decomposed by unique microorganisms living in the human intestines after ingestion, resulting in no pharmacological effect. Therefore, ginsenosides must be decomposed by microorganisms living in the intestines so as to be absorbed into the human body in the form of small molecules. Among these ginsenosides, ginsenosides Rb1, Rb2, Rc, and Rd are used by being metabolized by intestinal bacteria and bioconverted into compound K (IH·901), which has the greatest anticancer effect and is in use. Since the metabolism of drugs in the body varies depending on the individual's living environment or eating habits, the pharmacological effects of ginsenosides, the indicator ingredient, vary greatly even when the same amount of ginseng is taken. In order to neutralize these biological conversions in human metabolism, it is essential to convert ginsenosides to the required ginsenosides prior to administration to the human body.

In the preparation method of red or black color ginseng on the market, the number of times of steaming and the temperature and time for steaming are all different for every company. There is no standard for the content of bioactive ingredients contained in ginseng, and in some cases, there is a problem in that benzopyrene, a toxic substance, is detected. Thus, changes in physicochemical properties, processing processes, and quality standards need to be set. Accordingly, Korean Patent Registration No. 1972083 describes a black color ginseng preparing process in which the steaming process for steaming ginseng at 90° C. to 95° C. for 3 to 5 hours and drying steamed ginseng at a relatively low temperature of about 50° C. for 6 hours is repeated 3 to 4 times in total. This method has been adopted as a standardized process guideline for black color ginseng preparation in Korea, but there is still a problem in that functional ingredients are not sufficiently contained in the prepared black color ginseng.

COVID-10 is a disease that was first identified in Wuhan, the capital of China's Hubei province, at the end of 2019 and which has spread worldwide, resulting in a progressive pandemic, and is an infectious disease caused by SARS-CoV-2. The virus spreads from person to person mainly during close contact, sometimes through droplets from coughing, sneezing, and talking. The virus is most contagious during the first 3 days after symptom onset and may spread before symptoms appear or even at the end of the disease. The standard method for diagnosing COVID-19 uses real-time reverse transcription polymerase chain reaction (rRT-PCR) from a nasopharyngeal swab.

Meanwhile, various medications for COVID-19 are currently being developed, but these are mainly developed using compounds or existing medicines, and there has not yet been any medication developed using natural substances. These medications are not effective and also have side effects. Therefore, there is an increasing need for the development of excellent new medications for COVID-19 which have excellent infection inhibitory effects and low toxicity to prevent the outbreak of COVID-19 and treat COVID-19.

With this background, the present inventors have continuously made efforts to find an economical and safe method for improving the preparation of fermented black color ginseng containing functional ingredients at high contents, and as a result, they have developed a method for improving the preparation of fermented black color ginseng which is economical and safe, since the preparation process takes 7 to 15 days and benzopyrene is not detected in the fermented black color ginseng, by preparing the fermented black color ginseng through fermentation using a novel *Aspergillus niger* KHNT-1 strain isolated from fermented soybean powder, steaming utilizing pottery as a steamer, and drying (fermentation) utilizing a medical LED as a dryer/fermenter. In addition, it has been confirmed that fermented black color ginseng prepared by the method contains ginsenosides Rg3, Rg5, and Rk1, and OK at high contents and is effective against coronavirus, thereby completing the present invention.

DISCLOSURE

Technical Problem

An object of the present invention is to provide a novel *Aspergillus niger* KHNT-1 strain deposited under accession number KCTC14739BP.

Another object of the present invention is to provide a method for improving preparation of fermented black color ginseng, which includes a) a pretreatment step of washing and drying a fresh ginseng raw material; b) a step of immersing the fresh ginseng in an *Aspergillus niger* KHNT-1 strain culture solution and fermenting the fresh ginseng; and c) a step of repeating steaming and drying nine times after the fermentation step.

Still another object of the present invention is to provide fermented black color ginseng containing ginsenosides Rg5, Rg3, and Rk1, and Compound K (CK), which is prepared by the method described above.

Still another object of the present invention is to provide a pharmaceutical composition for preventing or treating coronavirus infectious disease, which contains the fermented black color ginseng as an active ingredient.

Still another object of the present invention is to provide a food composition for preventing or improving coronavirus infectious disease, which contains the fermented black color ginseng as an active ingredient.

Still another object of the present invention is to provide a feed composition for preventing or improving coronavirus infectious disease, which contains the fermented black color ginseng as an active ingredient.

Technical Solution

Each description and embodiment disclosed in this disclosure may also be applied to other descriptions and embodiments. That is, all combinations of various elements disclosed in this disclosure fall within the scope of the present invention. Further, the scope of the present invention is not limited by the specific description below.

An aspect of the present invention provides a novel *Aspergillus niger* KHNT-1 strain deposited under accession number KCTC14739BP.

In the present invention, the strain has been isolated from fermented soybean powder and identified, confirmed to be a novel strain through sequencing and phylogenetic tree analysis, named *Aspergillus niger* KHNT-1, deposited with the Korean Collection for Type Cultures KCTC), Korea Research Institute of Bioscience and Biotechnology (KRIBB), 181, Ipsin-gil, Jeongeup-si, Jeollabuk-do 56212, Republic of Korea, an international depository authority under the Budapest Treaty on Oct. 21, 2021, and given accession number KCTC14739BP. All restrictions imposed by the depositor on the availability to the public of the deposited material will be irrevocably removed upon the granting of the patent.

In the present invention, the strain is activated in response to light.

In the present invention, the term "*Aspergillus niger*" is a very common *Aspergillus* belonging to the genus *Aspergillus*, and is a fungus that grows well in soil or bread, fruits, nuts and the like, *Aspergillus niger* causes allergic reactions in some patients, but belongs to a relatively safe mold that does not significantly affect healthy people.

Another aspect of the present invention provides a method for improving the preparation of fermented black color ginseng containing functional ingredients at high contents. Specifically, there is provided a method for improving the preparation of fermented black color ginseng, which includes a) a pretreatment step of washing and drying a fresh ginseng raw material; b) a step of immersing the fresh ginseng in an *Aspergillus niger* KHNT-1 strain culture solution and fermenting the fresh ginseng; and c) a step of repeating steaming and drying nine times after the fermentation step.

The *Aspergillus niger* is as described above.

As a specific preparation method, the pretreatment step of a) may mean a preliminary drying process of washing fresh ginseng and drying the fresh ginseng at 40° C. to 50° C. to remove water. The immersion and fermentation step of b) is a process of simultaneously performing 5 to 9 hours of immersion and fermentation in a culture solution in which a novel *Aspergillus niger* KHNT-1 strain that has been isolated from fermented soybean powder and identified has been cultured, in the steaming step of c), steaming is performed by placing the fresh ginseng after the step b) in pottery, and applying heat to the pottery to raise the internal temperature of the pottery and thus to raise the temperature of water contained in the fresh ginseng itself. Specifically, the steaming step of c) may be performed at 75° C. to 90° C. for 5 to 9 hours. After the steaming step of c), the primarily steamed fresh ginseng may be immersed in the *Aspergillus Niger* KHNT-1 strain culture solution again, and then the drying step of d) may be performed. The drying is performed by utilizing a medical LED as a dryer, may be a step in which the fresh ginseng immersed again in the strain culture solution is fermented, and may be performed at 27° C. to 38° C. for 5 to 9 hours. By repeating steps c) and d) including the step of immersing the primarily dried fresh ginseng in the strain culture solution additionally 8 times, fermented black color ginseng through nine times of steaming and nine times of drying can be prepared, but the preparation method is not limited thereto.

In the present invention, as the drying method in the pretreatment step, various methods such as far-infrared ray drying, vacuum drying, freeze drying, drying in a sunny spot, drying in the shade, vacuum drying, and natural drying may be used, but the drying method is not limited thereto, and may specifically mean natural drying.

In the present invention, the steaming utilizing pottery is steaming by the water contained in fresh ginseng itself. Activation of far-infrared rays of 1 wavelengths, and the like by exposure of minerals due to heat dissipation of the pottery maximizes the change of saponin, so fermented black color ginseng can contain ginsenosides at higher contents than fermented black color ginseng prepared by an existing method.

In the present invention, as the drying method in c), various methods such as far-infrared ray drying, vacuum drying, freeze drying, drying in a sunny spot, drying in the shade, vacuum drying, hot air drying, natural drying, and drying utilizing an LED may be used, but the drying method is not limited thereto. Specifically, drying was performed utilizing an LED in the present invention.

The drying utilizing an LED may be to use the light-responsive feature of *Aspergillus niger*, and may also refer to a method for replacing the natural drying method.

In a preparation example of the present invention, an LED was manufactured to be most similar to solar radiation, containing not only the visible ray region of 440 nm to 780 nm but also the near-infrared rays of 850 nm and white wavelengths but excluding the ultraviolet region of 400 nm or less. More specifically, the LED may contain white wavelengths of 3000 K and 5500 K, and short wavelengths of 590 nm, 620 nm, 630 nm, and 850 nm, but is not limited thereto.

In the step of drying (fermenting) ginseng utilizing an LED manufactured by applying wavelengths similar to solar radiation, *Aspergillus niger* KHNT-1 may be activated to produce ginsenosides Rg5, Rg3, and Rk1, and CK at high contents.

In an example of the present invention, in order to examine the efficacy of *Aspergillus niger* KHNT-1 activation and increases in ginsenoside contents by drying utilizing an LED, when the ginsenoside content in fermented black color ginseng prepared through treatment with the strain and drying utilizing an LED is compared to those in fermented black color ginseng prepared through treatment with *Lactobacillus plantarum* and drying utilizing an LED (Comparative Example 1), fermented black color ginseng prepared through treatment with drinking water instead of treatment with a strain and drying utilizing an LED (Comparative Example 2), fermented black color ginseng prepared through no treatment and drying utilizing an LED (Comparative Example 3), and fermented black color ginseng prepared through treatment with *Aspergillus niger* KHNT-1 and general drying (Comparative Example 4), it has been confirmed that the total amount of ginsenosides in the fermented black color ginseng prepared by the method for improving the preparation of fermented black color ginseng according to the present invention is about 42 mg/g and the ginsenoside content is increased by 55%, 48%, 38%, and 330% or more compared to those of Comparative Examples 1 to 4, respectively.

In the present invention, the term "high content" means that a certain component is contained in a large amount. For the purpose of the present invention, the high content may mean that a large amount of ginsenoside, components are contained, and may mean that ginsenoside components are contained at higher contents than those produced by the existing preparation method, the treatment with other strains other than the strain of the present invention, and the like by specifically 100% or more, more specifically 50% or more, still more specifically 10% or more, but is not limited thereto.

In the present invention, the term "functional (ingredient)" means a physiological function, and may mean a physiological action that regulates various actions in our body. For the purpose of the present invention, the functional ingredient may mean specifically ginsenosides, more specifically ginsenosides Rg3, Rg5, and Rk1, and CK, but is not limited thereto.

In the present invention, the term "fermented black color ginseng" may mean dark brown or blackish brown black color ginseng prepared through a process of repeating a steaming and drying step in which fresh ginseng is steamed, cooked, and dried at least three times, usually nine times (nine times of steaming and nine times of drying), the process for preparing black color ginseng including a step of introducing an *Aspergillus* or the like into the fresh ginseng and fermenting the fresh ginseng. In the present invention, the fermented black color ginseng is prepared by performing fermentation using the novel *Aspergillus niger* KHNT-1 strain in the process of nine times of steaming and nine times of drying.

In the present invention, as the strain, any strain capable of producing fermented black color ginseng may be used, specifically, aspergiiii such as *Aspergillus oryzae* and *Aspergillus luchuensis*, yeasts such as *Saccharomyces cerevisiae*, and Lactic acid bacteria such as *Lactobacillus* and *Bifidobacterium* may be used, but the strain may mean *Aspergillus niger* for the purpose of the present invention, more specifically may mean *Aspergillus niger* KHNT-1.

In the present invention, the term "fresh ginseng" refers to ginseng that has not been processed after harvest, and is also called raw ginseng. As can be inferred from the name fresh ginseng, fresh ginseng contains water at around 75%.

In the present invention, as the fresh ginseng, commercially available fresh ginseng may be purchased and used, or fresh ginseng collected in nature or cultivated may be used, but the fresh ginseng is not limited thereto.

In the present invention, the term "immersion" means an operation to dip a material in various liquids so that the liquid adheres to the surface or penetrates into the inside. In the present invention, the immersion may mean immersing fresh ginseng in a strain culture solution for a certain period of time so that the culture solution penetrates into the inside of the fresh ginseng.

In the present invention, the term "fermentation" means a phenomenon in which chemical changes occur in organic substances by the action of microorganisms, in the present invention, the fermentation may mean decomposition of high molecular weight ginsenosides into low molecular weight ginsenosides that are easily absorbed into the human body, using the *Aspergillus niger* KHNT-1 strain.

In the present invention, the term "steaming" refers to steaming fresh ginseng or dried ginseng to cook the fresh ginseng, and means a process for steaming fresh ginseng to convert the fresh ginseng into black color ginseng for the purpose of the present invention. In the present invention, a method in which fresh ginseng is steamed by water contained in the fresh ginseng itself utilizing pottery as a steamer is adopted, but the steaming is not limited thereto.

Still another aspect of the present invention provides fermented black color ginseng containing ginsenosides Rg3, Rg5, and Rk1, and CK (Compound K), which is prepared by the method described above.

The fermented black color ginseng is as described above.

In the present invention, the term "ginsenosides" collectively refer to steroid saponins and triterpene saponins that are specifically present in *Panax*. The fermented black color ginseng prepared by the preparation method of the present invention contains ginsenosides Rg3, Rg5, and Rk1, and CK.

In the present invention, the term "Rg3" is a major ginsenoside contained in red ginseng and black color ginseng, and has been reported to have the effect of inhibiting neurodegenerative symptoms and anti-cancer anti-diabetic effects by inhibiting inflammatory neurotoxicity and anti-inflammatory activity. "Ra5" is a major ginsenoside component contained in steamed ginseng, red ginseng and black color ginseng like Rg3, and has been reported to have a pulmonary inflammation and neuroinflammation inhibitory effect and be effective in skin inflammatory response. "Rk1" is a ginsenoside that has the lowest molecular structure along with Compound K among ginsenosides contained in black color ginseng, and has been reported to be effective in anticancer, memory improvement, platelet aggregation inhibition and the like. "Compound K (CK)" is a physiologically active substance known to have immune enhancing action, tumor angiogenesis inhibitory action, and cancer cell invasion inhibitory action, and is closely related to the absorption rate of red ginseng and black color ginseng in the human body.

In the fermented black color ginseng according to the present invention, benzopyrene is not detected. Normally, as the number of times of steaming and drying increases, there may be a problem in terms of safety because of benzopyrene. According to the preparation method of the present invention, it has been confirmed that benzopyrene, is not detected even in fermented black color ginseng prepared through 14 times of steaming (FIG. 3B).

This suggests that the preparation method of the present invention, including steaming utilizing pottery and special wavelengths of LED, is a method that maximizes safety in the preparation of black color ginseng.

The term "benzopyrene" is a yellow crystalline solid belonging to the group of polycyclic aromatic hydrocarbons (PAHs), is known to be produced by incomplete combustion when carbohydrates, proteins, lipids and the like in food are decomposed at a temperature of 300° C. to 600° C., and is classified as a Class 1 human carcinogen. In recent red ginseng and black color ginseng preparing methods, studies on minimization of benzopyrene have been continuously reported.

In an experimental example of the present invention, it has been confirmed that benzopyrene is not contained in the fermented black color ginseng of the present invention (FIG. 3).

Still another aspect of the present invention provides a pharmaceutical composition for preventing or treating coronavirus infectious disease, which contains the fermented black color ginseng as an active ingredient.

The fermented black color ginseng is as described above.

In the present invention, the term "coronavirus" is a generic term for RNA viruses belonging to the family Coronaviridae, and causes respiratory and digestive infections in humans and animals. Coronavirus is easily infected mainly by mucosal transmission or droplet transmission, and generally causes mild respiratory infections in humans, but may also cause fatal infections, and causes diarrhea in cattle and pigs and respiratory disease in chickens. Coronavirus is a representative virus that causes fatal infectious diseases in modern civilization. In April 2003, Severe Acute Respiratory Syndrome, also known as SARS, was prevalent in the People's Republic of China, with a mortality rate of 9.6%, resulting in a large number of deaths. In 2015, Middle East Respiratory Syndrome, also known as MFRS, spread from the Middle East to the world with a mortality rate of about 36%, resulting in a large number of deaths. Since December 2019, as the new coronavirus infectious disease (Corona 19, COVID-19) from Wuhan, China, caused by SARS-CoV-2, has spread around the world, the number of infected people is increasing, and the fatality rate is as low as 2.6% according to data compiled until February 2020, but the number of confirmed cases is increasing worldwide and is ongoing. In the present invention, the coronavirus may specifically mean SARS-CoV-2, but is not limited thereto.

In the present invention, the term "prevention" refers to any action that inhibit or delay coronavirus infectious disease by administration of a composition containing fermented black color ginseng containing ginsenosides Rg5, Rg3, and Rk1, and CK at high contents.

In the present invention, the term "treatment" refers to any action in which symptoms of coronavirus infectious disease are improved or beneficially changed by administration of a composition containing a fermented black color ginseng extract containing ginsenosides Rg5, Rg3, and Rk1, and CK at high contents.

The pharmaceutical composition of the present invention may contain the fermented black color ginseng extract at 0.001% to 80% by weight, specifically 0.001% to 70% by weight, more specifically 0.001% to 60% by weight with respect to the total weight of the composition, but is not limited thereto.

The pharmaceutical composition may further contain a pharmaceutically acceptable carrier, excipient or diluent commonly used in the preparation of pharmaceutical compositions, and the carrier may include a non-naturally occurring carrier. The carrier, excipient and diluent include lactose, dextrose, sucrose, sorbitol, mannitol, xylitol, erythritol, maltitol, starch, gum acacia, alginate, gelatin, calcium phosphate, calcium silicate; cellulose, methyl cellulose, microcrystalline cellulose, polyvinyl pyrrolidone, water, methyl hydroxybenzoate, propyl hydroxybenzoate, talc, magnesium stearate and mineral oil.

Each of the pharmaceutical compositions may be formulated and used in the form of a tablet, pill; powder, granule, capsule; suspension, oral liquid, emulsion; syrup, sterilized aqueous solution, non-aqueous solution, suspension, emulsion, freeze-dried preparation, percutaneous absorbent, gel, lotion, ointment, cream, patch, cataplasma, paste, spray, skin emulsion, skin suspension, transdermal delivery patch, drug-containing bandage or suppository according to conventional methods. Specifically, in the case of being formulated, the preparation may be prepared using a commonly used diluent or excipient, such as a filler, a weighting agent, a binder, a wetting agent, a disintegrant, or a surfactant. The solid preparation for oral administration includes, but is not limited to, a tablet, a pill, a powder, a granule; a capsule and the like. Such a solid preparation may be prepared by mixing at least one or more excipients, for example, starch, calcium carbonate, sucrose, lactose, and gelatin. In addition to simple excipients, lubricants such as magnesium stearate and talc may also be used. The preparation may be prepared by adding various excipients, for example, wetting agents, sweeteners, flavoring agents, and preservatives, in addition to liquids and liquid paraffin for oral use. The preparation for parenteral administration includes a sterilized aqueous solution, a non-aqueous solvent, a suspension, an emulsion, a freeze-dried preparation and a suppository. Propylene glycol, polyethylene glycol, vegetable oils such as olive oil, and injectable esters such as ethyl oleate may be used as a non-aqueous solvent and a suspending agent. As a base for the suppository, Witepsol, Macrogol, Tureen 61, cacao butter, Laurin, glycerogelatin, and the like may be used.

In an example of the present invention, the infection inhibitory efficacy of fermented black color ginseng extract against SARS-CoV-2 using Vero E6 cells has been evaluated, and as a result, the fermented black color ginseng extract has exhibited a strong inhibitory effect to be about 6 times and about 1.8 times those of the positive control groups, remdesivir and chloroquine, respectively. In particular, the fermented black color ginseng extract at a concentration of 5 μg/mL or more has exhibited activity dose to 100%, and thus an infection inhibitory effect against the virus has been confirmed (FIG. 6A).

In another example, the intracellular replication inhibitory efficacy of fermented black color ginseng extract against SARS-CoV-2 using Vero E6 cells has been evaluated, and as a result, it has been confirmed that the fermented black color ginseng extract inhibits the proliferation of SARS-CoV-2 in a concentration dependent manner, and in particular, the fermented black color ginseng extract at a concentration of 25 μg/mL exhibits a similar level of activity to that of remdesivir (FIG. 6B).

Therefore, it can be expected that fermented black color ginseng containing ginsenosides Rg5, Rg3, and Rk1, and CK at high contents, which is prepared by the method of the present invention can be effectively used for preventing or treating coronavirus infectious disease.

Still another aspect of the present invention for achieving the object provides a food composition for preventing or improving coronavirus infectious disease, which contains fermented black color ginseng as an active ingredient.

The terms, fermented black color ginseng, coronavirus and prevention are as described above.

In the present invention, the term "food" includes meat, sausage, bread, chocolate, candy, snacks, confectionery, pizza, ramen, other noodles, chewing gum, dairy products including ice cream, various soups, beverages, tea, drinks, alcoholic beverages, vitamin complexes, health functional foods, health foods, and the like, and includes all foods in a conventional sense.

Since the food composition of the present invention is derived from ginseng, which can be consumed daily, can be expected to have a high anti-coronavirus effect, and thus may be used greatly usefully for health promotion purposes.

The health functional food is the same term as food for special health use (FoSHU), and means food having high medical and remedial effects, which is processed to efficiently have bioregulatory function in addition to nutritional supply. Here, 'functionality' means obtaining useful effects for health purposes, such as adjusting nutrients for the structure and function of the human body or physiological actions. The food of the present invention may be prepared by a method commonly used in the art, and may be prepared by adding raw materials and ingredients commonly added in the art at the time of preparation. The food may be prepared in any formulation without limitation as long as it is a formulation recognized as food.

The food composition of the present invention may be prepared in various forms of formulations, has an advantage of not having side effects that may occur when drugs are taken for a long period of time since a natural substance is used as the raw material unlike general drugs, and has excellent portability, and thus the food of the present invention may be consumed as an adjuvant to enhance the anti-coronavirus effect.

The health food means food that has an active health maintenance or promotion effect compared to general food, and health supplement food means food for the purpose of supplementing health. In some cases, the terms health functional food, health food, and health supplement food are used interchangeably.

Specifically, the health functional food is food prepared by adding the composition of the present invention to food materials such as beverages, teas, spices, chewing gum, confectionery or the like or encapsulating, powdering, suspending or the like the composition, means to bring about a specific health effect when ingested, and has the advantage of not having side effects that may occur when drugs are taken for a long period of time since food is used as the raw material unlike general drugs.

The food composition may further contain a physiologically acceptable carrier, and the kind of carrier is not particularly limited, and any carrier commonly used in the art may be used.

The food composition may contain additional ingredients that are commonly used in food compositions and may improve odor, taste, and vision. For example, vitamins A, C, D, E, B1, B2, B6, and B12, niacin, biotin, folate, pantothenic add, and the like may be contained. In addition, minerals such as zinc (Zn), iron (Fe), calcium (Ca), chromium (Cr), magnesium (Mg), manganese (Mn), copper (Cu), and chrome (Cr); and amino adds such as lysine, tryptophan, cysteine, and valine may be contained.

The food composition may contain food additives such as a preservative (potassium sorbate, sodium benzoate, salicylic add, sodium dehydroacetate or the like), a bactericide (bleaching powder, high bleaching powder, sodium hypochlorite or the like), an antioxidant (butylhydroxyanisole (BHA), butylhydroxytoluene (BHT) or the like), a coloring agent (tar colorant or the like); a color coupler (sodium nitrite, sodium nitrite or the like), a bleaching agent (sodium sulfite), a seasoning (MSG sodium glutamate or the like), a sweetener (dulcin, sodium cyclamate, sodium saccharin or the like), a flavoring agent (vanillin, Factories or the like), an expanding agent (alum, D-potassium hydrogen tartrate or the like), a strengthening agent, an emulsifying agent, a thickening agent (thickener), a coating agent, a gum base agent, a foam inhibitor, a solvent, and an improver. The additives may be selected depending on the kind of food and used in an appropriate amount.

As an example, the food composition of the present invention may be used as a health drink composition. In this case, the health drink composition may contain various flavoring agents, natural carbohydrates and the like as additional ingredients as in conventional beverages. The aforementioned natural carbohydrates may be monosaccharides such as glucose and fructose; disaccharides such as maltose and sucrose; polysaccharides such as dextrins and cyclodextrins; or sugar alcohols such as xylitol, sorbitol, and erythritol. As sweeteners, natural sweeteners such as thaumatin and stevia extract; and synthetic sweeteners such as saccharin and aspartame may be used. The ratio of the natural carbohydrates may be generally about 0.01 g to 0.04 g, specifically about 0.02 g to 0.03 g per 100 mL of the health drink composition of the present invention.

In addition to the above, the health drink composition may contain various nutrients, vitamins, electrolytes, flavors; coloring agents, pectic acid; salts of pectic acid, alginic add, salts of alginic add, organic adds, protective colloidal thickeners, pH adjusters, stabilizers, preservatives, glycerin, alcohols or carbonating agents, and the like. In addition to the above, the health drink composition may contain fruit flesh for preparing natural fruit juice, fruit juice beverage, or vegetable beverage. These ingredients may be used independently or in combination.

The ratio of these additives is not greatly important, but is generally selected in the range of 0.01 to 0.1 parts by weight per 100 parts by weight of the health drink composition of the present invention.

In the present invention, the term "improvement" refers to any action that at least reduces a parameter, for example, the severity of symptom associated with the condition being treated by administration of the food composition according to the present invention.

Still another aspect of the present invention provides a feed composition for preventing or improving coronavirus infectious disease, which contains fermented black color ginseng as an active ingredient.

The terms, fermented black color ginseng, coronavirus, prevention and improvement are as described above.

The fermented black color ginseng according to the present invention exhibits an excellent anti-coronavirus effect, and may be contained in a feed composition for the purpose of preventing or improving coronavirus infectious disease. Since the feed composition can be consumed by animals on a daily basis, a high effect may be expected for the prevention or improvement of coronavirus infectious disease.

In the present invention, the term "feed" means any natural or artificial diet, meal or the like for an animal to eat, ingest, and digest or suitable for eating, ingesting, and digesting or an ingredient of the meal. Subjects to which the feed composition of the present invention may be applied are not particularly limited, and the feed composition may be applied to any form. The feed composition may be applied to animals such as chickens, pigs, monkeys, dogs, cats, rabbits, guinea pigs, rats, mice, cows, sheep, and goats without limitation.

The kind of feed is not particularly limited, and feed commonly used in the art may be used. Non-limiting examples of the feed include vegetable feed such as grains, root fruits, food processing by-products, algae, fibers, pharmaceutical by-products, oils and fats, starches, gourd or grain by-products; and animal feed such as proteins, inorganic materials, oils and fats, mineral oils, oils and fats, single cell proteins, zooplankton, or food. These may be used singly or in mixture of two or more thereof.

The fermented black color ginseng extract or physiologically acceptable salt thereof of the present invention contained in the feed composition of the present invention may vary depending on the purpose and conditions of use of the feed, and as an example, may be contained at 0.01% to 100% by weight, more specifically 1% to 80% by weight with respect to the total weight of the feed composition.

Advantageous Effects

According to the economical and safe method for improving the preparation of fermented black color ginseng, the fermented black color ginseng is prepared through fermentation using the novel *Aspergillus niger* KHNT-1 strain according to the present invention, steaming utilizing pottery as a steamer, and drying (fermentation) utilizing a medical LED as a dryer/fermenter, and the fermented black color ginseng contains ginsenosides Rg3, Rg5, and Rk1, and OK at high contents, and can be usefully utilized as a high value-added new drug raw material that is required to be contained at a high content per unit and in the field of high-functional food development.

BRIEF DESCRIPTION OF DRAWINGS

FIG. 1 illustrates the phylogenetic tree analysis of a novel *Aspergillus niger* KHNT-1 strain;

FIG. 2 is a schematic diagram of an improved process for preparing fermented black color ginseng of the present invention;

FIG. 3 is test certificates confirming that benzopyrene is not detected in fermented black color ginseng prepared through nine times of steaming and nine times of drying (FIG. 3A) and fermented black color ginseng prepared through 14 times of steaming and 14 times of drying (FIG. 38);

FIG. 4 is test certificates confirming that there is a ginsenoside content Increasing effect in a case where treatment with an *Aspergillus niger* KHNT-1 strain and drying treatment utilizing an LED (FIG. 4A) are performed as compared to cases where treatment with *Lactobacillus plantarum* strain and drying treatment utilizing an LED (FIG. 48), treatment with drinking water instead of treatment with a strain and drying treatment utilizing an LED (FIG. 40), no treatment and drying treatment utilizing an LED (FIG. 4D), and treatment with an *Aspergillus* nicer KHNT-1 strain and general drying treatment (FIG. 4E) are performed, respectively.

FIG. 5 is a graph illustrating the results of cytotoxicity evaluation at various concentrations of fermented black color ginseng extract; and FIG. 6 is a graphs illustrating the evaluation results of infection inhibitory efficacy (FIG. 6A) and replication inhibitory efficacy (FIG. 68) of fermented black color ginseng extract against SARS-CoV-2.

DETAILED DESCRIPTION OF THE INVENTION

Hereinafter, the present invention will be described in more detail with reference to Examples. These Examples are intended to explain the present invention in more detail, and the scope of the present invention is not limited by these Examples.

Experimental Example 1. Isolation and Identification of Microorganisms

The strain used in the present invention was isolated from fermented soybean (meju) powder.

Specifically, water extract was taken from dry fermented soybeans using 10 mL water, and then 100 μL of the extract diluted by serial dilution was carefully cultured at 30° C. for 2 days using a Potato Dextrose Agar (PDA) plate. Thereafter, different colony types were selected, and strains forming a single colony were selected and further subcultured on a new PDA under the same conditions. The cultured strain was preserved in POB containing 30% glycerol and stored at −70° C. for use in experiments.

Experimental Example 2. Sequencing and Phylogenetic Tree Analysis

The phylogenetic tree analysis was performed using sequencing of the selected strain.

Specifically, the internal transcribed spacer (TS) region of 18 S rDNA was amplified using universal primers through an automated DNA sequencing system (Applied Biosystems, Foster City, CA, USA) from Macrogen, Seoul, Korea. The obtained PCR product was initially sequenced and identified by performing homology search using the online tool BLAST (https://blast.ncbi.nlm.nih.gov/Blast.cqi), and was designated as *A. niger*_MT804610.1.

Based on the similarity search with the 163 ribosomal RNA sequence of *A. niger* MT804610.1 identified above in the GenBank database, phylogenetic tree analysis was performed using the closest organism and a partial sequence (1693 bp) of the identified strain. The phylogenetic tree was constructed by way of the maximum likelihood method using MEGA X (Molecular Evolutionary Genetic Analysis, version 10.1).

As a result, as illustrated in Fla 1, it has been confirmed that the identified strain designated as *A. niger*_MT804610.1 shows a bootstrap value of 92% with *A. niger*_MF093522.1 and forms a duster.

This was named *Aspergillus niger* KHNT-1 and was used in the present invention.

Experimental Example 3. Detection of Benzopyrene

The benzopyrene content in the fermented black odor ginseng prepared was analyzed based on the Food and Drug Administration (2007) Guidelines for testing benzo(a)pyrene in health functional foods (so-called black color ginseng) (KFDA Public Health Functional Food Standards Team-5454, 2007, 12, 31).

Experimental Example 4. Preparation of Cell Line and Virus

Experiments on the inhibitory efficacy on the novel BARS-Coil-2 were performed using vero cells, and the vero cells used in the present invention were cultured in Dulbecco's modified Eagle's medium (DMEM, Welgene, Gyeongsan, Korea) containing American Type Culture Collection (ATCC, CCL-81; Manassas, VA) 10% heat-inactivated fetal bovine serum and 1× Antibiotic-Antimycotic (Gibcol-Thermo Fisher Scientific, Waltham, MA) at 37° C. and 5% carbon dioxide.

SARS-COV-2 (BetaCoV/Korea/DCDC03/2020) was provided by the National Pathogen Resource Bank of the Korea Centers for Disease Control and Prevention.

Preparation Example 1. Method for Preparing Fermented Black Color Ginseng

Fermented black color ginseng was prepared by performing steaming nine times and drying nine times after a pretreatment step of washing and drying a fresh ginseng raw material and an immersion and fermentation step using the strain identified in the Experimental Example above.

Specifically, fresh ginseng raw material was pretreated by washing and drying at 40° C. to 50° C., and the fresh ginseng was immersed and fermented in an *Aspergillus niger* KHNT-1 strain culture solution for 5 to 9 hours, then treated with the strain, fermented, and placed in pottery. Heat was applied to raise the internal temperature of the pottery to 75° C. to 90° C. and thus to raise the temperature of water contained in the fresh ginseng itself, and steaming was performed for 5 to 9 hours. Thereafter, a step of performing immersion in the strain culture solution for 5 to 9 hours and then drying and fermentation at 27° C. to 38° C. for 5 to 9 hours utilizing a medical LED as a dryer was repeated nine times, whereby fermented black color ginseng was prepared (FIG. 2).

Example 1 and Comparative Examples 1 to 4. Microbial Activating and Ginsenoside Content Increasing Effect by Drying Utilizing LED The effect of drying by LED utilized in the preparation process of fermented black color ginseng of the present invention on *Aspergillus niger* KHNT-1 strain and ginsenoside content was investigated.

Specifically, fermented black color ginseng prepared by treating fresh ginseng with *Aspergillus niger* KHNT-1 and drying and fermenting the fresh ginseng utilizing an LED to which short wavelengths of 590 nm, 620 nm, 630 nm, and 850 nm and white wavelengths of 3000 K and 5500 K were applied was denoted as Example 1. Fermented black color ginseng prepared by treating fresh ginseng with *Lactobacillus plantarum* and drying and fermenting the fresh ginseng utilizing the LED was denoted as Comparative Example 1. Fermented black color ginseng prepared by treating fresh ginseng with drinking water instead of a strain and drying the fresh ginseng utilizing the LED was denoted as Comparative Example 2. Fermented black color ginseng prepared by drying fresh ginseng utilizing the LED without any treatment was denoted as Comparative Example 3. Fermented black color ginseng prepared by treating fresh ginseng with *Aspergillus niger* KHNT-1 and drying the fresh ginseng by way of a general drying method was denoted as Comparative Example 4. The ginsenoside contents therein are shown in Table 1 below.

TABLE 1

| Ingredients | Example 1 Treatment with KHNT-1 and drying utilizing LED | Comparative Example 1 Treatment with *Lactobacillus* and drying utilizing LED | Comparative Example 2 Treatment with water and drying utilizing LED | Comparative Example 3 Without treatment and drying utilizing LED | Comparative Example 4 Treatment with KHNT-1 and general drying |
|---|---|---|---|---|---|
| Rg3(S) | 9,245.49 | 7,634.60 | 6,274.20 | 7,752.09 | 2,533.39 |
| Rg3(R) | 4,961.90 | 3,380.41 | 3,757.48 | 3,248.11 | 2,042.42 |
| C-K | 34.10 | 26.48 | 32.21 | 52.27 | 29.26 |
| Rk1 | 11,764.54 | 6,425.42 | 7,151.53 | 8,009.52 | 1,999.41 |
| Rg5 | 16,346.40 | 9,756.40 | 11,246.04 | 11,566.93 | 3,262.77 |
| Total | 42,352.43 | 27,223.31 | 28,461.46 | 30,628.92 | 9,867.25 |

It has been confirmed that benzopyrene is not detected at all not only in the fermented black color ginseng of the present invention prepared through steaming nine times and drying nine times by way of the method including a step of performing drying at a low temperature utilizing an LED as a dryer, but also in the fermented black color ginseng prepared through steaming 14 times and drying 14 times by way of the preparation method (FIGS. 3A and 3B).

Preparation Example 2. Manufacture of Solar Radiation-Like LED

As a method to replace the natural drying method, an LED containing all of the solar radiation spectrum was manufactured and utilized in the drying and fermentation step of the present invention.

Specifically, the LED was manufactured to be most similar to the solar radiation containing all wavelengths including the visible ray region of 440 nm to 780 nm as well as the near-infrared rays of 850 nm and white wavelengths (including 3000 K and 5500 K) but excluding the ultraviolet region of 400 nm or less.

As a result, as illustrated in FIG. 4 and Table 1, it has been confirmed that the total amount of ginsenosides in fermented black color ginseng prepared through treatment with *Aspergillus niger* KHNT-1 and drying utilizing an LED is about 42 mg/g, and this means that the ginsenoside content is increased by about 55%, about 48%, and about 38% or more, respectively, compared to those of Comparative Examples 1 to 3, and thus the effect of treatment with the strain of the present invention on the ginsenoside content has been confirmed. In addition, the effect of drying utilizing an LED on the increase in ginsenoside content in Comparative Example 4 was examined, and as a result, it has been confirmed that the ginsenoside content in Example 1 is significantly increased by about 330% or more compared to that in Comparative Example 4.

Therefore, it has been confirmed that the fermented black color ginseng prepared through treatment with *Aspergillus niger* KHNT-1 and drying utilizing an LED of the present invention contains functional ingredients at significantly high contents since the total amount of ginsenosides Rg3, Rk1, and Rg5, and CK in the fermented black color ginseng is about 42 mg/g.

Example 2. Evaluation of Cytotoxicity

Cytotoxicity of fermented black color ginseng extract was examined using Vero E6 cells. At this time, DMEM medium containing penicillin/streptomycin and 10% fetal bovine serum was used for the cells. The cells were inoculated into a 96-well plate at $5\times10^4$ cells/well, and cultured for 24 hours in an incubator at 37° C. and 5% $CO_2$. After 24 hours, the cells were treated with the fermented black color ginseng extract at a concentration of 1 μg/mL, 5 μg/mL, or 25 μg/mL and cultured again for 24 hours in an incubator at 37° C. and 5% $CO_2$. After 24 hours, the supernatant was removed, the cells were treated with 100 μL of 0.5 mg/mL. MTT reagent and cultured for 1 hour, the supernatant was removed, the cells were treated with 100 μL of DMSO, and after 10 minutes, the absorbance was measured at 540 nm using a microplate reader.

As a result, as Illustrated in FIG. 5, it has been confirmed that the cell viability of 100% is maintained at all concentrations.

Example 3. Anti-Coronavirus Efficacy of Fermented Black Color or Ginseng Containing Ginsenosides Rg3, Rg5, and Rk1, and CK at High Contents Example 3-1. Evaluation of Infection Inhibitory Efficacy Against SARS-CoV-2

In order to examine whether the fermented black color ginseng extract interfares with cell penetration of SARS-CoV-2, the plaque formation inhibitory efficacy of the virus was evaluated.

Specifically, the Vero E6 cell line was inoculated into a 12-well plate at $3\times10^5$ cells/well and cultured for 24 hours in an incubator at 37° C. and 5% $CO_2$, the supernatant was removed, and washing with PBS was performed two times. The cell line was treated with fermented black color ginseng extract at a concentration of 1 μg/mL, 5 μg/mL, or 25 μg/mL in the SARS-CoV-2 (50 pfu/well) absorption step and cultured for 1 hour in an incubator at 37° C. and 5% $CO_2$. The supernatant was then removed, and washing with PBS was performed two times. The cells were overlaid with 0.6% agarose in DMEM containing 0.3% BSA, and the 12-well plate was cultured for 3 days in an incubator at 37° C. and 5% $CO_2$. Thereafter, the cells were stained with 0.4% crystal violet for 10 minutes, washed with PBS three times to remove the virus and extract, and additionally overlaid with agarose, and then the plaque formation inhibitory ability of SARS-CoV-2 was examined. The plague reduction rate was compared between cells treated with SARS-CoV-2 and those not treated with SARS-CoV-2. The evaluation was repeated three times, and statistical analysis was performed using Graph Pad Prism 5 software. At this time, student's t-test method was used for the standard error.

As a result, as illustrated in FIG. 6A, the fermented black color ginseng (FBCG) extract at a concentration of 1 μg/mL has exhibited a strong inhibitory effect to be about 6 times and about 1.8 times those of the positive control groups, remdesivir (Rem) and chloroquine (CP), respectively. In particular, activity close to 100% has been confirmed in the fermented black color ginseng extract at a concentration of 5 μg/mL or more, and thus the strong antiviral effect of fermented black color ginseng extract against SARS-CoV-2 has been confirmed.

Example 3-2. Evaluation of Replication Inhibitory Efficacy Against SARS-CoV-2

In order to examine whether the fermented black color ginseng extract interfares with the intracellular replication of SARS-CoV-2, the viral genes in the cell culture solution were quantitatively analyzed through rea-time PCR.

Specifically, the Vero E6 cell line was inoculated into a 12-well plate at $3\times10^5$ cells/well and cultured for 24 hours in an incubator at 37° C. and 5% $CO_2$. Thereafter, the supernatant was removed, and washing with PBS was performed two times. The cells were infected with SARS-CoV-2 at 0.01 mol and cultured for 1 hour in an incubator at 5% $CO_2$. After 1 hour of viral infection, the cells were treated with fermented black color ginseng extract at a concentration of 1 μg/mL, 5 μg/mL, or 25 μg/mL and cultured for 24 hours in an incubator at 37° C. and 5% $CO_2$. In order to obtain an RNA sample, virus-infected cells were treated with fermented black color ginseng extract, the cells and supernatant were collected after 18 hours, RNA was extracted, and the level of viral gene expression was examined through real-time PCR.

As a result, as illustrated in FIG. 6B, it has been confirmed that the fermented black color ginseng extract inhibits the proliferation of SARS-CoV-2 in a concentration dependent manner, and a similar level of activity to that in remdesivir is exhibited in the fermented black color ginseng extract at a concentration of 25 μg/mL.

Through this, the inhibitory efficacy of fermented black color ginseng containing ginsenosides Rg3, Rg5, and Rk1, and CK at high contents, which is prepared by the preparation method of the present invention, on the infection stage of SARS-CoV-2 into host cells and the proliferation after infection into host cells has been confirmed.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the present invention is defined by the appended claims rather than by the description preceding them, and therefore all changes and modifications that fall within metes and bounds of the claims or equivalents of such metes and bounds are therefore intended to be embraced by the claims.

The invention claimed is:

1. A method for improving preparation of fermented black color ginseng, the method comprising:

a) a pretreatment step of washing and drying a fresh ginseng raw material;

b) a step of immersing the fresh ginseng in an *Aspergillus niger* KHNT-1 strain culture solution, wherein the *Aspergillus niger* KHNT-1 strain is deposited under accession number KCTC14739BP, and fermenting the fresh ginseng; and c) a step of repeating steaming and drying nine times after the fermentation step, wherein the steaming in step c) is performed by placing the fresh ginseng in pottery and applying heat to the pottery to raise an internal temperature of the pottery and to raise a temperature of water contained in the fresh ginseng, wherein after each steaming in step c), the fresh ginseng is immersed in the *Aspergillus niger* KHNT-1 strain culture solution, and wherein the drying in step c) is performed utilizing an LED as a dryer, the LED being manufactured to emit wavelengths similar to solar radiation containing a visible ray region of 440 nm to 780 nm and near-infrared rays of 850 nm and white wavelengths but excluding an ultraviolet region of 400 nm or less.

2. The method for improving preparation of fermented black color ginseng according to claim 1, wherein the drying step a) is performed at 40° C. to 50° C.

3. The method for improving preparation of fermented black color ginseng according to claim 1, wherein the immersion and fermentation in a strain culture solution of b) is performed for 5 to 9 hours.

4. The method for improving preparation of fermented black color ginseng according to claim 1, wherein the pottery emits far-infrared rays due to exposure of minerals contained in the pottery to heat during the steaming in step c).

5. The method for improving preparation of fermented black color ginseng according to claim 1, wherein the steaming in c) is performed at 75° C. to 90° C. for 5 to 9 hours.

6. The method for improving preparation of fermented black color ginseng according to claim 1, wherein the drying in c) is performed at 27° C. to 38° C. for 5 to 9 hours.

7. The method for improving preparation of fermented black color ginseng according to claim 1, wherein the LED further emits light of 3000 K and 5500 K and short wavelengths of 590 nm, 620 nm, 630 nm, and 850 nm.

8. The method for improving preparation of fermented black color ginseng according to claim 7, wherein the wavelengths emitted by the LED activate the *Aspergillus niger* KHNT-1 strain to produce ginsenosides Rg5, Rg3, and Rk1, and Compound K.

9. The method for improving preparation of fermented black color ginseng according to claim 1, wherein benzopyrene is not detected in the fermented black color ginseng.

* * * * *